United States Patent [19]

Berka et al.

[11] Patent Number: 5,981,243

[45] Date of Patent: Nov. 9, 1999

[54] PURIFIED MYCELIOPHTHORA LACCASES AND NUCLEIC ACIDS ENCODING SAME

[76] Inventors: Randy Michael Berka, 3609 Modoc Pl.; Stephen H. Brown, 3708 Miwok Pl., both of Davis, Calif. 95616; Feng Xu, 1534 Carmel Valley Dr., Woodland, Calif. 95776; Palle Schneider, Rydtoften 43, DK-2750 Ballerup, Denmark; Karen M. Oxenbøll, Slotsvej 76, DK-2920 Charlottenlund, Denmark; Dorrit A. Aaslyng, DK-3500 Vaeloese, Gartnerkrogen 69, Denmark

[21] Appl. No.: 08/939,218

[22] Filed: Sep. 29, 1997

Related U.S. Application Data

[60] Division of application No. 08/441,146, May 15, 1995, abandoned, which is a continuation-in-part of application No. 08/253,781, Jun. 3, 1994, abandoned.

[51] Int. Cl.[6] .............................. C12N 9/02; C12N 15/53; C09B 69/00
[52] U.S. Cl. ................................ 435/189; 8/401; 536/23.2
[58] Field of Search ................................ 435/189; 8/401; 536/23.2

[56] References Cited

U.S. PATENT DOCUMENTS 3,251,742  5/1966  Soloway ..................................... 167/88
5,770,418  6/1998  Yaver et al. ............................. 435/189

FOREIGN PATENT DOCUMENTS 0 504 005 A1  3/1992  European Pat. Off. .
91/05839  5/1991  WIPO .

OTHER PUBLICATIONS

Berka et al., Abstracts of Papers, BIOT 196, vol. 209, No. 1–2,1995.

Germann et al., The Journal of Biological Chemistry, vol. 263, No. 2, pp. 885–896, 1988.

J. Rogalski et al., "Affinity Cromotography as a Rapid and Convenient Method for Purification of Fungal Laccases", Biotechnol. Bioengineering 37(8): 770–777, 1991.

J. Bollag et al., "Comparative Studies of Extracellular Fungal Laccases", Appl. Environ. Microbiol. 48(4): 849–854 Oct. 1984.

C.R. Perry et al. "Identification of Two Laccase Genes in the Cultivated Mushroom Agaricus bisporus", J. Gen. Microbiol. 139: 1209–1218, 1993.

S. Kawai et al., "Cloning and Sequence Ananlysis of Laccase Genes and Construction of a Host–Vector System in Coriolus versicolor", J. Cell Biochem Suppl. 17 Part C: 192, 1993.

C.F. Thurston, "The Structure and Function of Fungal Laccases", Microbiol. 140 (Pt 1): 19–26, 1994.

J.P. Geiger et al., "Laccase of Rigidoporus lignosus and Phellinus noxious", Appl Biochem. Biotechnol. 12(2): 121–133, Apr. 1986.

*Primary Examiner*—Rebecca E. Prouty
*Attorney, Agent, or Firm*—Steve T. Zelson; Reza Green; Robert L. Starnes

[57] ABSTRACT

The present invention relates to isolated nucleic acid constructs containing a sequence encoding a Myceliophthora laccase, and the laccase proteins encoded thereby.

18 Claims, 6 Drawing Sheets

FIG. 2A

```
gctagctcttggtcacgtcgtttcgcccgccccctccttcaaccccctgagtagtcggctaagcgatcctca      80
atctggtcttgtgaggtcacgtcctccagcagatgacagttcatcgagcgagtgatctccaccaccagaagggaggggg  160
gatgcgcgcatgctccaacatccctgttgtcgctagagacgtcgcggcatcagcctttcatcacacgagcacgtccac  240
ggaccggctcctttcacccccgcgtcctccggagattgagtcacgatatttcgggatgtgggaaggggagagaaagga  320
gggggaggggcggaaacatgttggatacgagctgcgccccttttcaacatcgagaacaggaagtcgttggtgtcggcc  400
gtaatgtctataaaacgaggctcctctcgtcgtccttcttcggtctctctcgtccacaccaagccagtcttg        480
cctgagccacctgagccacttcaactcatcatcttcagtcaagtcgttcattgacattgtgtctctttctatcgagt  560
cggcttcccggccctcaccacaacATGAAGTCCTTCATCAGCGCCGACGCTTTGGTGGGCATTCTCACCCCTAGCG  640
                        MetLysSerPheIleSerAlaAlaThrLeuLeuValGlyIleLeuThrProSerV  -29
TTGCTGCTGCCCCTCCATCCACCCTGAGCAGCGCGACCTGCTCGTCCCGATCACGGAGGAGGCAGCCGTGAAG      720
alAlaAlaAlaProProSerThrProGluGlnArgAspLeuLeuValProIleThrGluGluAlaAlaValLys       -3
GCTCGGCCAGCAGAGCTGCAACACCCCAGCAACCGGGCGTGCTGGACTGACGGATACGACATCAACACGACTACGAAGT  800
AlaArgGlnSerCysAsnArgAlaCysTrpThrAspThrAspIleAsnThrAspTyrGluVa                  25
GGACAGCCCGGACACGGGTGTTCGGCCGtgagtgctctcgttaattacgcttcggcgagttgcgcagatatta      880
lAspSerProAspThrGlyValArgPro                                                    35
atactgcaaacctaagcaggagctgacagTACACTCTGACTCTCACCGAAGTCGACAACTGGACCGGACCTGA      960
                             TyrThrLeuThrLeuThrGluValAspAsnTrpThrGlyProAs       50
```

FIG. 2B

```
TGGCGTCGTCAAGGAGAAGGTCATGCTGGTTAACAgtacggcacccctttcttgtcctaggatctggtgatgtgcgtc  1040
pGlyValValLysGluLysValMetLeuValAsnA                                              62 gttgccctgagagagactgaccgagcctttggctgcagATAGTATAATCgtaattaattataccgccctgctccagc   1120
                                       snSerIleIleG                              66 agccccagcagctcgagaagggtatctgaagttagtcaggcctgacctgaccgggccaaccaccatagGACCAAC     1200
                                                                   lyProTh       68 gttgcccctgagagagactgaccgagcctttggctgcagtATAGTATAATCgtaattaattataccgccctgctccagc 1280
rIlePheAlaAspTrpGlyAspThrIleGlnValThrValIleAsnAsnLeuGluThrAsnGl                  89 tctcttgctctcctcgtccgcgactaataataatcaactcgtgtggaaaacagCACGTCGATCCACTGGCACGGACTG  1360
                                                     yThrSerIleHisTrpHisGlyLeu   97

CACCAGAAGGGCACCAACCTGCACGGCGCCAAGGGTATCACCGAGTGCCCGATCCCCGCCAAGGGAGGAGGAAGGT    1440
HisGlnLysGlyThrAsnLeuHisAspGlyAlaAsnGlyIleThrGluThrCysProIleProProLysGlyArgLysVa 124

GTACCGGTTCAAGGCTCAGCAGTACGGACGAGTCTGGTACCACTCGCACTTCTCGGCCCAGTACGGCAACGGCGTGTCG 1520
lTyrArgPheLysAlaGlnGlnTyrGlyThrSerTrpTyrHisSerHisPheSerAlaGlnTyrGlyAsnGlyValValG 151

GGGCCATTCAGATCAACGGCGGCCCTCGCGTCCGTACGACACCGGCGTGTTCCCATCAGCGACTACTACTAC       1600
lyAlaIleGlnIleAsnGlyProAlaSerLeuProTyrAspThrAspThrAspThrAspThrThrThrThrThr       177

AGCTCGGCCGACGAGCTGGTGGAACTCACCAAGAACTCGGCGCCCTTCAGCGACAACGTCCTGTTCAACGGCACGGC   1680
SerSerAlaAspGluLeuValGluLeuThrLysAsnSerGlyAlaProPheSerAspAsnValLeuPheAsnGlyThrAl 204
```

FIG. 2C

```
CAAGCACCCGGAGAGACGGGCGAGGGCGAGTACGCCAACGTGACGCTCACCCCGGGCCGGGGCACCCGGCCTGATCA  1760
aLysHisProGluThrGlyGluGlyGluTyrAlaAsnValThrLeuThrProGlyArgArgHisArgLeuIleA    231

ACACGTCGGTCGAGAACCACTTCCAGTCTCGCTCGTCAACCACACACGACCATCATGCCGCCGACATGGTGCCCGTC  1840
snThrSerValGluAsnHisPheGlnValSerLeuValAsnHisThrMetThrIleIleAlaAlaAspMetValProVal  257

AACGCCATGACGGTCGACAGCCTCTTCCTCGGCGTCGGCCAGCGCTACGATGTCGTCATCGAAGCCAGCCGAACGCCCGG  1920
AsnAlaMetThrValAspSerLeuPheLeuGlyValGlyGlnArgTyrAspValValIleGluAlaSerArgThrProGl  284

GAACTACTGGTTTAACGTCACATTGGCGGGCGGCCTGCTCTGCGGCGGCCTCCAGGAATCCCTACCCGGCCGCCATCTTCC  2000
yAsnTyrTrpPheAsnValThrPheGlyGlyGlyLeuLeuCysGlyGlySerArgAsnProTyrProAlaAlaIlePheH  311

ACTACGCCGGGGCGCCCCGGCGGCGACGAGGGCAAGGCCCCGGTCGACCTGCTGACCACAACTGCCTGACCTCCCCAAC  2080
isTyrAlaGlyAlaProGlyGlyAspGluGlyLysAlaProValAspHisAsnCysLeuAspLeuProAsn  337

CTCAAGCCCGTCGTGGCCCTGGCCCGCGACGTGCCCCTGAGCGGCTTCGCCGACACACGTCGACTGCACCCTGA  2160
LeuLysProValValAlaArgaspValProLeuSerGlyPheAlaLysArgProAspAsnThrLeuAspValThrLeuAs  364

CACCACGGGCACGCCCCTGTTCTGTCTGGAAGGTCAACGCCAGCCCCATCAACATGACTGGGCAGGCCCGTCGTCGACT  2240
pThrThrGlyThrProLeuPheValTrpLysValAsnGlySerAlaIleAsnIleAspTrpGlyArgProValValAspT  391

ACGTCCTCACGCAGAACACCAGCTTCCCACCCGGGTACAACATTGTCGAGGTGAACGGAGCTGATCAGGtaagaaaaagg  2320
yrValLeuThrGlnAsnThrSerPheProProGlyTyrAsnIleValGluValAsnGlyAlaAspGln                413 ggaccgcaggggtgctgctgcaagtacacccttgctcgccctcctgttcctcttccttaataactacctcccaaccctcccccc  2400 taattaattcacttaaaggccgatcaagactgaccgagcccctctcttgcagTGGTCGTACTGGTTGATCGAGAACG  2480
                                                    TrpSerTyrTrpLeuIleGlnAsnA   422
```

FIG. 2D

```
ATCCCGGGCCACCTTTCACCCTACCGCATCCGATGCACCTGCAC gtaagttggatacatatatatatatatacatt    2560
spProGlyAlaProPheThrLeuProHisProMetHisLeuHis                                      436 gctttcctggctcgctccctaaataaataacaaaataacaaaaataacaaaaaaagGGCCACGACTTTTACGTGCTGGG   2640
                                                        GlyHisAspPheTyrValLeuGl   444

CCGCTCGCCCGACGAGTCGCCGCATCCAACGAGCGGCACGTGTTCGATCCGGCCCTGCTGAGCGGGG               2720
yArgSerProAspGluSerProAlaSerAsnGluArgHisValPheAspProAlaArgLeuLeuSerGlyA            471

CCAACCCTGTGCGGGACGTGACGATGCTGCCCGGTTCGGGTGGGTTCGGGGCCGACAACCCGGGC                 2800
laAsnProValArgArgAspValSerMetLeuProAlaPheGlyTrpValValLeuAlaPheArgAlaAspAsnProGly   497

GCCTGGCTGTTCCACTGCCACATCGCCTGGCACGTCTCGGGCGGCCTGGGCGTCGTCTACCTCGAGCGCCGACGACCT   2880
AlaTrpLeuPheHisCysHisIleAlaTrpHisValSerGlyGlyLeuGlyValValTyrLeuGluArgAlaAspAspLe   524

GCGCGGGGGCCGTCGACGCCGAGCGCCGAGACCTCGCCCTCGCCGACGCCGACTGGCCGCCTACTGGCCTACCAACC    2960
uArgGlyAlaValSerAspAlaAspLeuAspAspArgLeuCysAlaAspTrpArgArgTyrArgTrpProThrAsnP     551

CCTACCCCAAGTCCGACTCGGGCCTCAAGCACCACCGCTGGGTCGAGGAGGGCGAGTGGCTGGTCAAGGCGtgagcgaaggag   3040
roTyrProLysSerAspSerGlyLeuLysHisHisArgTrpValGluGluGlyGluTrpLeuValLysAla*** gaaaaggaaacaaagagggggggggggctagtcctatttttgcttttttttgtccttgtccttgtgctggcggt   3120 tacctggtaaaggagaaggggggcccaagttcgagtggtgtgtgatcgggtaaatattatc                     3183
```

PURIFIED MYCELIOPHTHORA LACCASES AND NUCLEIC ACIDS ENCODING SAME

CROSS-REFERENCE TO RELATED APPLICATIONS

This application is a divisional of U.S. application Ser. No. 08/441,146 filed May 15, 1995, now abandoned, which a continuation-in-part of application Ser. No. 08/253,781 filed Jun. 3, 1994, now abandoned, the contents of which are fully incorporated herein by reference.

FIELD OF THE INVENTION

The present invention relates to isolated nucleic acid fragments encoding a fungal oxidoreductase enzyme and the purified enzymes produced thereby. More particularly, the invention relates to nucleic acid fragments encoding a phenol oxidase, specifically a laccase, of a thermophilic ascomycete, Myceliophthora.

BACKGROUND OF THE INVENTION

Laccases (benzenediol:oxygen oxidoreductases) are multi-copper-containing enzymes that catalyze the oxidation of phenolics. Laccase-mediated oxidations result in the production of aryloxy-radical intermediates from suitable phenolic substrate; the ultimate coupling of the intermediates so produced provides a combination of dimeric, oligomeric, and polymeric reaction products. Such reactions are important in nature in biosynthetic pathways which lead to the formation of melanin, alkaloids, toxins, lignins, and humic acids. Laccases are produced by a wide variety of fungi, including ascomycetes such as Aspergillus, Neurospora, and Podospora, the deuteromycete Botrytis, and basidiomycetes such as Collybia, Fomes, Lentinus, Pleurotus, Trametes, and perfect forms of Rhizoctonia. Laccase exhibits a wide range of substrate specificity, and each different fungal laccase usually differs only quantitatively from others in its ability to oxidize phenolic substrates. Because of the substrate diversity, laccases generally have found many potential industrial applications. Among these are lignin modification, paper strengthening, dye transfer inhibition in detergents, phenol polymerization, juice manufacture, phenol resin production, and waste water treatment.

Although the catalytic capabilities are similar, laccases made by different fungal species do have different temperature and pH optima, and these may also differ depending on the specific substrate. A number of these fungal laccases have been isolated, and the genes for several of these have been cloned. For example, Choi et al. (Mol. Plant-Microbe Interactions 5: 119–128, 1992) describe the molecular characterization and cloning of the gene encoding the laccase of the chestnut blight fungus, *Cryphonectria parasitica*. Kojima et al. (J. Biol. Chem. 265: 15224–15230, 1990; JP 2-238885) provide a description of two allelic forms of the laccase of the white-rot basidiomycete *Coriolus hirsutus*. Germann and Lerch (Experientia 41: 801,1985; PNAS USA 83: 8854–8858, 1986) have reported the cloning and partial sequencing of the *Neurospora crassa* laccase gene. Saloheimo et al. (J. Gen. Microbiol. 137: 1537–1544, 1985; WO 92/01046) have disclosed a structural analysis of the laccase gene from the fungus *Phlebia radiata*.

Attempts to express laccase genes in heterologous fungal systems frequently give very low yields(Kojima et al., supra; Saloheimo et al., Bio/Technol. 9: 987–990, 1991). For example, heterologous expression of *Phlebia radiata* laccase in *Trichoderma reesei* gave only 20 mg per liter of active enzyme(Saloheimo, 1991, supra). Although laccases have great commercial potential, the ability to express the enzyme in significant quantities is critical to their commercial utility. At the present time there are no laccases which are expressed at high levels in commercially utilized hosts such as Aspergillus. Thus, the need exists for a laccase which can be produced in commercially useful (i.e., gram per liter or more) quantities. The present invention fulfills such a need.

SUMMARY OF THE INVENTION

The present invention relates to a DNA construct containing a nucleic acid sequence encoding a Myceliophthora laccase. The invention also relates to an isolated laccase encoded by the nucleic acid sequence. Preferably, the laccase is substantially pure. By "substantially pure" is meant a laccase which is essentially (i.e., $\geq 90\%$) free of other non-laccase proteins.

In order to facilitate production of the novel laccase, the invention also provides vectors and host cells comprising the claimed nucleic acid sequence, which vectors and host cells are useful in recombinant production of the laccase. The sequence is operably linked to transcription and translation signals capable of directing expression of the laccase protein in the host cell of choice. A preferred host cell is a fungal cell, most preferably of the genus Aspergillus. Recombinant production of the laccase of the invention is achieved by culturing a host cell transformed or transfected with the construct of the invention, or progeny thereof, under conditions suitable for expression of the laccase protein, and recovering the laccase protein from the culture.

The laccases of the present invention are useful in a number of industrial processes in which oxidation of phenolics is required. These processes include lignin manipulation, juice manufacture, phenol polymerization and phenol resin production.

BRIEF DESCRIPTION OF THE FIGURES

FIG. 2 illustrates the nucleotide (SEQ ID NO: 1) and amino acid (SEQ ID NO: 2) sequence of *Myceliophthora thermophila* laccase. Lower case letters in the nucleotide sequence indicate the position of introns. Putative TATA and CAAT sequences in the promoter region are in boldface and underlined. Consensus lariat structures(PuCTPuAC)within the introns are underlined.

DETAILED DESCRIPTION OF THE INVENTION

*Myceliophthora thermophila* is a thermophilic Ascomycete originally described by Apinis (Nova Hedwigia 5: 57–78, 1963) and named *Sporotrichum thermophile*. Subsequent taxonomic revisions have placed this organism in the genus Chrysosporium (Von Klopotek, A. Arch. Microbiol. 98: 365–369, 1974) and later to Myceliophthora (Van Oorschot, Persoonia 9: 401–408, 1977). A number of organisms known by other names also appear to belong to this species. These include *Sporotrichum cellulophilum* (U.S. Pat. No. 4,106,989); *Thielavia thermophila* (Fergus and Sinden, Can. J. Botany 47: 1635–1637, 1968); *Chrysosporium fergussi* and *Corynascus thermoohilus* (Von Klopotek, supra). This species is known as a source of a number of different industrially useful enzymes, such as cellulases, β-glucosidase and xylanase (see, e.g., Oberson et al., Enzyme Microb. Technol. 14: 303–312, 1992; Merchant et al., Biotechnol. Lett. 10: 513–516, 1988; Breuil et al. Biotechnol. Lett. 8: 673–676, 1986; Gilbert et al., Bioresource Technol. 39: 147–154, 1992). It has now been determined that Myceliophthora produces a neutral pH laccase, and the gene encoding this laccase can be used to produce large yields of the enzyme in convenient host systems such as Aspergillus.

Figure 1:
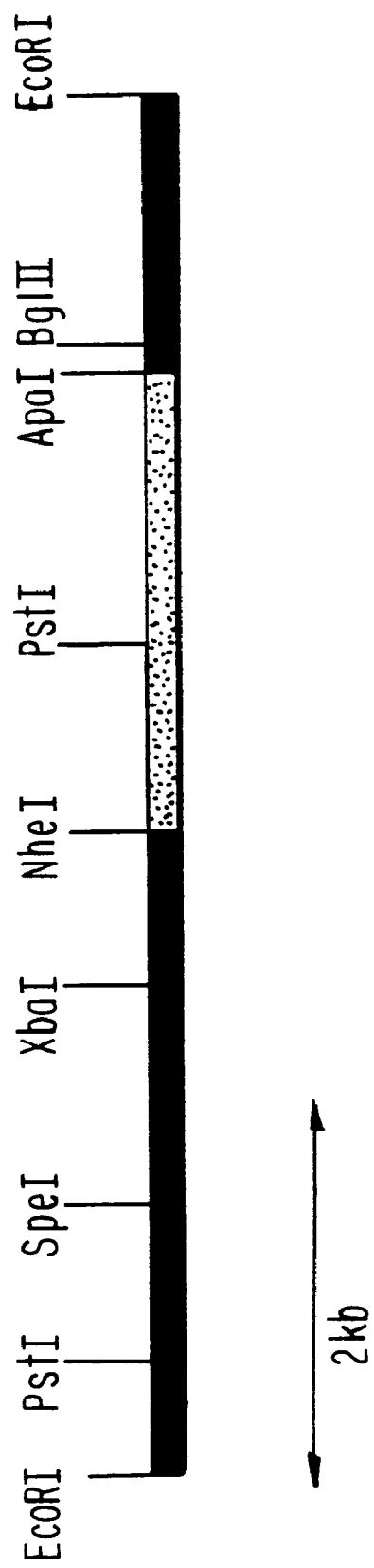
FIG. 1 shows a restriction map of a 7.5 EcoRI fragment in pRaMB1. The region hybridizing to the *N. crassa* laccase gene probe is shaded.

To identify the presence of a laccase gene in Myceliophthora, a 5' portion of the *Neurospora crassa* laccase gene(lcc1) is used as a probe, under conditions of mild stringency, in southern hybridization of total genomic DNA of different fungal species. An approximately 12 kb laccase specific sequence is detected in the Myceliophthora DNA. The *N. crassa* fragment is then used to screen about 20,000 plaques of an *M. thermophila* genomic DNA library in a λ EMBL4 bacteriophage cloning vector. Eight plaques strongly hybridize with the probe; from these eight, DNA is isolated from three. Each of these clones contains a 7.5 EcoRI fragment which also hybridizes to the probe (FIG. 1). One of the fragments is subcloned into pBR322 to generate plasmid pRaMB1. Using the lcc1 probe, the position of the coding region of the clone is determined. The entire *M. thermophila* coding region appears to be contained with a 3.2 kb NheI-BglII segment, which is then cloned into pUC119 and sequenced by the primer walking method.

Once the sequence is determined, the positions of introns and exons within the gene is assigned based on alignment of the deduced amino acid sequence to the corresponding *N. crassa* laccase gene product. From this comparison, it appears that the gene (lccM) of *M. thermophila* is composed of seven exons(246, 79, 12, 70, 973, 69 and 411 nucleotides) interrupted by six introns (85, 84, 102, 72, 147, and 93 nucleotides). The coding region, excluding intervening sequences, is very GC-rich(65.5% G+C) and encoded a preproenzyme of 620 amino acids: a 22 amino acid signal peptide, a 25 amino acid propeptide, and a mature laccase comprising 573 amino acids. The sequence of the *M. thermophila* gene and the predicted amino acid sequence is shown in FIG. 2 (SEQ ID NOS: 1 and 2).

The laccase gene is then used to create an expression vector for transformation of Aspergillus host cells. The vector, pRaMB5 contains the *A. oryzae* TAKA-amylase promoter and terminator regions. The construction of pRaMB5 is outlined in FIG. 3. Aspergillus cells are cotransformed with the expression vector and a plasmid containing the pyrG or amdS selectable marker. Transformants are selected on the appropriate selective medium containing ABTS. Laccase-producing colonies exhibit a green halo and are readily isolatable. Selected transformants are grown up in shake flasks and culture broths tested for laccase activity by the syringaldazine method. Shake flask cultures are capable of is producing 0.2 or more g/liter of laccase, and in fermentors, yields of over 1–2 g/liter are observed.

According to the invention, a Myceliophthora gene encoding a laccase can be obtained by methods described above, or any alternative methods known in the art, using the information provided herein. The gene can be expressed, in active form, using an expression vector. A useful expression vector contains an element that permits stable integration of the vector into the host cell genome or autonomous replication of the vector in a host cell independent of the genome of the host cell, and preferably one or more phenotypic markers which permit easy selection of transformed host cells. The expression vector may also include control sequences encoding a promoter, ribosome binding site, translation initiation signal, and, optionally, a repressor gene or various activator genes. To permit the secretion of the expressed protein nucleotides encoding a signal sequence may be inserted prior to the coding sequence of the gene. For expression under the direction of control sequences, a laccase gene to be used according to the invention is operably linked to the control sequences in the proper reading frame. Promoter sequences that can be incorporated into plasmid vectors, and which can direct the transcription of the laccase gene, include but are not limited to the prokaryotic β-lactamase promoter (Villa-Kamaroff, et al., 1978, Proc. Natl. Acad. Sci. U.S.A. 75:3727–3731) and the tac promoter (DeBoer, et al., 1983, Proc. Natl. Acad. Sci. U.S.A. 80:21–25). Further references can also be found in "Useful proteins from recombinant bacteria" in Scientific American, 1980, 242:74–94; and in Sambrook et al., Molecular Cloning, 1989.

The expression vector carrying the DNA construct of the invention may be any vector which may conveniently be subjected to recombinant DNA procedures, and the choice of vector will typically depend on the host cell into which it is to be introduced. Thus, the vector may be an autonomously replicating vector, i.e. a vector which exists as an extrachromosomal entity, the replication of which is independent of chromosomal replication, e.g. a plasmid, or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the laccase DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA construct of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliouefaciens* α-amylase (amyQ), or the promoters of the *Bacillus subtilis* xylA and xylB genes. In a yeast host, a useful promoter is the eno-1 promoter. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A. awamori* glucoamylase (glaA), *Rhizomucor miehei* lipase, *A. oryzae* alkaline protease, *A. oryzae* triose phosphate isomerase or *A. nidulans* acetamidase. Preferred are the TAKA-amylase and glaA promoters.

The expression vector of the invention may also comprise a suitable transcription terminator and, in eukaryotes, polyadenylation sequences operably connected to the DNA sequence encoding the laccase of the invention. Termination and polyadenylation sequences may suitably be derived from the same sources as the promoter. The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, cheniformis, or one which confers antibiotic resistance such as ampicillin, kanamycin, chloramphenicol or tetracycline resistance. Examples of Aspergillus selection markers include amdS, pyrG, argB, niaD, sC, and hygB, a marker giving rise to hygromycin resistance. Preferred for use in an Aspergillus host cell are the amdS and pyrG markers of *A. nidulans* or *A. oryzae*. A frequently used mammalian marker is the dihydrofolate reductase (DHFR) gene. Furthermore, selection may be accomplished by co-transformation, e.g. as described in WO 91/17243.

It is generally preferred that the expression gives rise to a product which is extracellular. The laccases of the present invention may thus comprise a preregion permitting secretion of the expressed protein into the culture medium. If desirable, this preregion may be native to the laccase of the invention or substituted with a different preregion or signal sequence, conveniently accomplished by substitution of the DNA sequences encoding the respective preregions. For example, the preregion may be derived from a glucoamylase or an amylase gene from an Aspergillus species, an amylase gene from a Bacillus species, a lipase or proteinase gene from *Rhizomucor miehei*, the gene for the α-factor from *Saccharomyces cerevisiae* or the calf preprochymosin gene. Particularly preferred, when the host is a fungal cell, is the preregion for *A. oryzae* TAKA amylase, *A. niger* neutral amylase, the maltogenic amylase form Bacillus NCIB 11837, *B. stearothermophilus* α-amylase, or *Bacillus licheniformis* subtilisin. An effective signal sequence is the *A. oryzae* TAKA amylase signal, the *Rhizomucor miehei* aspartic proteinase signal and the *Rhizomucor miehei* lipase signal.

The procedures used to ligate the DNA construct of the invention, the promoter, terminator and other elements, respectively, and to insert them into suitable vectors containing the information necessary for replication, are well known to persons skilled in the art (cf., for instance, Sambrook et al. Molecular Cloning, 1989).

The cell of the invention either comprising a DNA construct or an expression vector of the invention as defined above is advantageously used as a host cell in the recombinant production of a enzyme of the invention. The cell may be transformed with the DNA construct of the invention, conveniently by integrating the DNA construct in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The host cell may be selected from prokaryotic cells, such as bacterial cells. Examples of suitable bacteria are gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulars, Bacillus lautus, Bacillus megatenium, Bacillus thuringiensis,* or *Streptomyces lividans* or *Streptomyces murinus*, or gram negative bacteria such as *E. coli*. The transformation of the bacteria may for instance be effected by protoplast transformation or by using competent cells in a manner known per se.

The host cell may also be a eukaryote, such as mammalian cells, insect cells, plant cells or preferably fungal cells, including yeast and filamentous fungi. For example, useful mammalian cells include CHO or COS cells. A yeast host cell may be selected from a species of Saccharomyces or Schizosaccharomyces, e.g. *Saccharomyces cerevisiae*. Useful filamentous fungi may selected from a species of Aspergillus, e.g. *Aspergillus oryzae* or *Aspergillus niger*. Alternatively, a strain of a Fusarium species, e.g. *F. oxysporum*, can be used as a host cell. Fungal cells may be transformed by a process involving protoplast formation and transformation of the protoplasts followed by regeneration of the cell wall in a manner known per se. A suitable procedure for transformation of Aspergillus host cells is described in EP 238 023. A suitable method of transforming Fusarium species is described by Malardier et al., 1989.

The present invention thus provides a method of producing a recombinant laccase of the invention, which method comprises cultivating a host cell as described above under conditions conducive to the production of the enzyme and recovering the enzyme from the cells and/or culture medium. The medium used to cultivate the cells may be any conventional medium suitable for growing the host cell in question and obtaining expression of the laccase of the invention. Suitable media are available from commercial suppliers or may be prepared according to published formulae (e.g. in catalogues of the American Type Culture Collection).

In a preferred embodiment, the recombinant production of laccase in culture is achieved in the presence of an excess amount of copper. Although trace metals added to the culture medium typically contain a small amount of copper, experiments conducted in connection with the present invention show that addition of a copper supplement to the medium can increase the yield of active enzyme many-fold. Preferably, the copper is added to the medium in soluble form, preferably in the foam of a soluble copper salt, such as copper chloride, copper sulfate, or copper acetate. The final concentration of copper in the medium should be in the range of from 0.2–2 mM, and preferably in the range of from 0.05–0.5 mM. This method can be used in enhancing the yield of any recombinantly produced fungal laccase, as well as other copper-containing enzymes, in particular oxidoreductases.

The resulting enzyme may be recovered from the medium by conventional procedures including separating the cells from the medium by centrifugation or filtration, precipitating the proteinaceous components of the supernatant or filtrate by means of a salt, e.g. ammonium sulphate, followed by purification by a variety of chromatographic procedures, e.g. ion exchange chromatography, gel filtration chromatography, affinity chromatography, or the like. Preferably, the isolated protein is about 90% pure as determined by SDS-PAGE, purity being most important in food, juice or detergent applications.

In a particularly preferred embodiment, the expression of laccase is achieved in a fungal host cell, such as Aspergillus. As described in detail in the following examples, the laccase gene is ligated into a plasmid containing the *Aspergillus oryzae* TAKA α-amylase promoter, and the *Aspergillus nidulans* amdS selectable marker. Alternatively, the amdS may be on a separate plasmid and used in co-transformation. The plasmid (or plasmids) is used to transform an Aspergillus species host cell, such as *A. oryzae* or *A. niger* in accordance with methods described in Yelton et al. (PNAS USA 81: 1470–1474,1984).

Those skilled in the art will recognize that the invention is not limited to use of the nucleic acid fragments specifically disclosed herein, for example, in FIG. 1. It will also be apparent that the invention encompasses those nucleotide sequences that encode the same amino acid sequences as depicted in FIG. 1, but which differ from the specifically depicted nucleotide sequences by virtue of the degeneracy of the genetic code. Also, reference to FIG. 1 in the specification and the claims will be understood to encompass both the genomic sequence depicted therein as well as the corresponding cDNA and RNA sequences, and the phrases "DNA construct" and "nucleic acid sequences" as used herein will be understood to encompass all such variations. "DNA construct" shall generally be understood to mean a DNA molecule, either single- or double-stranded, which may be isolated in partial form from a naturally occurring gene or which has been modified to contain segments of DNA which are combined and juxtaposed in a manner which would not otherwise exist in nature.

The Myceliophthora laccase described herein has a particularly high specific activity on a syringaldazine substrate relative to other known ascomycete or deuteromycete extracellular laccases in which such specific activity has been described. The present sequence provides a means by which other such ascomycete and/or deuteromycete laccases can also be isolated. Identification and isolation of laccase genes from sources other than those specifically exemplified herein can be achieved by utilization of the methodology described in the present examples, with publicly available ascomycete and deuteromycete strains. In particular, the specific sequence disclosed herein can be used to design primers and/or probes useful in isolating similar laccase genes by standard PCR or southern hybridization techniques. The present invention thus encompasses those ascomycete and deuteromycete laccases which have a specific activity of at least about 30 SOU/mg, and preferably at lease about 40 SOU/mg, "SOU" being defined as μmole of substrate oxidized per minute as measured with syringaldazine as a substrate, at optimum pH.

In addition, the invention also encompasses other Myceliophthora laccases, including alternate forms of laccase which may be found in *M. thermophila* and as well as laccases which may be found in other fungi falling within - the definition of Myceliophthora as defined by Van Oorschot, 1977, supra. Identification and isolation of laccase genes from sources other than those specifically exemplified herein can be achieved by utilization of the methodology described in the preseent examples, with publicly available Myceliophthora strains. Alternately, the sequence disclosed herein can be used to design primers and/or probes useful in isolating laccase genes by standard PCR or southern hybridization techniques. Other named Myceliophthora species include *Myceliphthora hinnulea* (Awao et al., Mycotaxon. 16: 436–440, 1983), *Myceliophthora vellerea* (Guarro et al, Mycotaxon. 23: 419–427, 1985), and *Myceliophthora lutea* Costatin. Also encompassed are laccases which are synonyms, e.g., anamorphs or perfect states of species or strains of the genus Myceliophthora. Strains of Myceliophthora are readily accessible to the public in a number of culture collections, such as ATCC 48102, 48103, 48104 et al.; CBS 117.65, 131.65, 379.65 et al., DSM 1799 (*M. thermophila*), ATCC 52474, CBS 539.82, 540.82 et al. (*M. hinnulea*), DSM 62114, CBS 146.50, 147.50, 157.51 et al (*M. lutea*), and CBS 478.76, 479.76 and 715.84 (*M. vellerea*). The invention also encompasses any variant nucleotide sequence, and the protein encoded thereby, which protein retains at least about an 80%, preferably at least 85%, and most preferably at least 90–95% homology with the amino acid sequence depicted in FIG. 2, and which qualitatively retains the laccase activity of the sequence described herein. Useful variants within the categories defined above include, for example, ones in which conservative amino acid substitutions have been made, which substitutions do not significantly affect the activity of the protein. By conservative substitution is meant that amino acids of the same class may be substituted by any other of that class. For example, the nonpolar aliphatic residues Ala, Val, Leu, and Ile may be interchanged, as may be the basic residues Lys and Arg, or the acidic residues Asp and Glu. Similarly, Ser and Thr are conservative substitutions for each other, as are Asn and Gln. It will be apparent to the skilled artisan that such substitutions can be made outside the regions critical to the function of, the molecule and still result in an active enzyme. Retention of the desired activity can readily be determined by conducting a standard ABTS oxidation method, such as is described in the present examples.

The protein can be used in number of different industrial processes. These processes include polymerization of lignin, both Kraft and lignosulfates, in solution, in order to produce a lignin with a higher molecular weight. A neutral/alkaline laccase is a particular advantage in that Kraft lignin is more soluble at higher pHs. Such methods are described in, for example, Jin et al., Holzforschung 45(6): 467–468, 1991; U.S. Pat. No. 4,432,921; EP 0 275 544; PCT/DK93/00217, 1992.

The laccase of the present invention can also be used for in-situ depolymerization of lignin in Kraft pulp, thereby producing a pulp with lower lignin content. This use of laccase is an improvement over the current use of chlorine for depolymerization of lignin, which leads to the production of chlorinated aromatic compounds, which are an environmentally undesirable by-product of paper mills. Such uses are described in, for example, Current opinion in Biotechnology 3: 261–266, 1992; J. Biotechnol. 25: 333–339, 1992; Hiroi et al., Svensk papperstidning 5: 162–166, 1976. Since the environment in a paper mill is typically alkaline, the present laccase is more useful for this purpose than other known laccases, which function best under acidic conditions.

Oxidation of dyes or dye precursors and other chromophoric compounds leads to decolorization of the compounds. Laccase can be used for this purpose, which can be particularly advantageous in a situation in which a dye transfer between fabrics is undesirable, e.g., in the textile industry and in the detergent industry. Methods for dye transfer inhibition and dye oxidation can be found in WO 92/01406; WO 92/18683; EP 0495836; Calvo, Mededelingen van de Faculteit Landbouw-wetenschappen/ Rijiksuniversitet Gent.56: 1565–1567, 1991; Tsujino et al., J. Soc. Chem.42: 273–282, 1991.

The laccase is particularly well-suited for use in hair dyeing. In such an application, the laccase is contacted with a dye precursor, preferably on the hair, whereby a controlled oxidation of the dye precursor is achieved to convert the precursor to a dye, or pigment producing compound, such as a quinoid compound. The dye precursor is preferably an aromatic compound belonging to one of three major chemical families: the diamines, aminophenols (or aminonaphthols) and the phenols. The dye precursors can be used alone or in combination. At least one of the intermediates in the copolymerization must be an ortho- or para-diamine or aminophenol(primary intermediate). Examples of such are found in Section IV, below, and include p-phenylene-diamine(pPD), p-toluylene-diamine, chloro-p-phenylenediamine, p-aminophenol, o-aminophenol. 3,4- diaminotoluene; additional compounds are also described in U.S. Pat. No. 3,251,742, the contents of which are incorporated herein by reference. In one embodiment, the starting materials include not only the enzyme and a primary intermediate, but also a modifier (coupler) or (or combination of modifiers), which modifier is typically a meta-diamine meta-aminophenol, or a polyphenol. Examples of modifier compounds include m-phenylene-diamine, 2,4-diaminoanisole, α-naphthol, hydroquinone, pyrocatechol, resorcinol. and 4-chlororesorcinol. The modifier then reacts with the primary intermediate in the presence of the laccase, converting it to a colored compound. In another embodiment, the laccase can be used with the primary intermediate directly, to oxidize it into a colored compound. In all cases, the dyeing process can be conducted with one or more primary intermediates, either alone or in combination with one or more modifiers. Amounts of components are in accordance with usual commercial amounts for similar components, and proportions of components may be varied accordingly.

The use of this laccase is an improvement over the more traditional use of $H_2O_2$, in that the latter can damage the hair, and its use usually requires a high pH, which is also damaging to the hair. In contrast, the reaction with laccase can be conducted at alkaline, neutral or even acidic pH, and the oxygen needed for oxidation comes from the air, rather than via harsh chemical oxidation. The result provided by the use of the Myceliophthora laccase is comparable to that achieved with use of $H_2O_2$, not only in color development, but also in wash stability and light fastness. An additional commercial advantage is that a single container package can be made containing both the laccase and the precursor, in an oxygen free atmosphere, which arrangement is not possible with the use of $H_2O_2$.

The present laccase can also be used for the polymerization of phenolic compounds present in liquids. An example of such utility is the treatment of juices, such as apple juice, so that the laccase will accelerate a precipitation of the phenolic compounds present in the juice, thereby producing a more stable juice. Such applications have been described in Stutz, Fruit processing 7/93, 248–252, 1993; Maier et al., Dt. Lebensmittel-rindschau 86(5): 137–142, 1990; Dietrich et al., Fluss. Obst 57(2): 67–73, 1990,.

Laccases such as the Myceliophthora laccase are also useful in soil detoxification (Nannipieri et al., J. Environ. Qual. 20: 510–517,1991; Dec and Bollag, Arch. Environ. Contam. Toxicol. 19: 543–550, 1990).

The invention is further illustrated by the following non-limiting examples.

EXAMPLES

I. ISOLATION OF *MYCELIOPHTHORA THERMOPHILA* LACCASE GENE

A. MATERIALS AND METHODS

1. DNA Extraction and Hybridization analysis

Total cellular DNA is extracted from fungal cells of *Myceliophthora thermophila* strain E421 grown 24 hours in 25 ml of YEG medium (0.5% yeast extract, 2% glucose) using the following protocol: mycelia are collected by filtration through Miracloth (Calbiochem) and washed once with 25 ml of TE buffer. Excess buffer is drained from the mycelia which are subsequently frozen in liquid nitrogen. Frozen mycelia are ground to a fine powder in an electric coffee grinder, and the powder added to 20 ml of TE buffer and 5 ml of 20% SDS (w/v) in a disposable plastic centrifuge tube. The mixture is gently inverted several times to ensure mixing, and extracted twice with an equal volume of phenol:chloroform:isoamyl alcohol (25:34:1). Sodium acetate (3M solution) is added to give a final concentration of 0.3 M and the nucleic acids are precipitated with 2.5 volumes of ice cold ethanol. The tubes are centrifuged at 15,000× g for 30 minutes and the pellet is allowed to air-dry for 30 minutes before resuspending in 0.5 ml of TE buffer. DNase-free ribonuclease A is added to a concentration of 100 µg/ml and the mixture is incubated at 37° C. for 30 minutes. Proteinase K (200 µg/ml) is added and each tube is incubated an additional one hour at 37° C. Finally, each sample is extracted twice with phenol:chloroform:isoamyl alcohol before precipitating the DNA with sodium acetate and ethanol. DNA pellets are dried under vacuum, resuspended in TE buffer, and stored at 4° C.

Total cellular DNA samples from transformants and an untransformed control strain are analyzed by Southern hybridization. Approximately 5 µg of DNA is digested with EcoRI and fractionated by size on a 1% agarose gel. The gel is photographed under short wavelength UV and soaked for 15 minutes in 0.5 M NaOH, 1.5 M NaCl followed by 15 minutes in 1 M Tris-HCl, pH 8, 1.5 M NaCl. DNA in the gel is transferred onto Zeta-Probe™ hybridization membrane (BioRad Laboratories) by capillary blotting in 20× SSPE (R. W. Davis et al., Advanced Bacterial Genetics, A Manual for Genetic Engineering. Cold Spring Harbor Press. 1980) Membranes are baked for 2 hours at 80° C. under vacuum and soaked for 2 hours in the following hybridization buffer at 45° C. with gentle agitation: 5× SSPE, 35% formamide (v/v), 0.3% SCS, 200 µg/ml denatured and sheared salmon testes DNA. The laccase-specific probe fragment (approx. 1.5 kb) encoding the 5'-portion of the *N. crassa* lcc1 gene is amplified from *N. crassa* genomic DNA using standard PCR conditions (Perkin-Elmer Cetus, Emeryville, Calif.) with the following pair of primers: forward primer, 5' CGAGACT-GATAACTGGCTTGG 3'; reverse primer, 5' ACGGCG-CATTGTCAGGGAAGT 3'. The amplified DNA segment is first cloned into a TA-cloning vector (Invitrogen, Inc., San Diego, Calif.), then purified by agarose gel electrophoresis following digestion with EcoRI. The purified probe fragment is radiolabeled by nick translation with $\alpha[^{32}P]dCTP$ (Amersham) and added to the hybridization buffer at an activity of approximately $1\times10^6$ cpm per ml of buffer. the mixture is incubated overnight at 45° C. in a shaking water bath. Following incubation, the membranes are washed once in 0.2× SSPE with 0.1% SDS at 45° C. followed by two washes in 0.2× SSPE (no SDS) at the same temperature. The membranes are allowed to dry on paper towels for 15 minutes, then wrapped in Saran Wrap™ and exposed to x-ray film overnight at −70° C. with intensifying screens (Kodak).

2. DNA Libraries and Identification of Laccase Clones

Genomic DNA libraries are constructed in the bacteriophage cloning vector λ-EMBL4(J. A. Sorge, in Vectors, A Survey of Molecular Cloning Vectors and Their Uses, Rodriguez et al., eds, pp.43–60, Butterworths, Boston, 1988). Briefly, total cellular DNA is partially digested with Sau3A and size-fractionated on low-melting point agarose gels. DNA fragments migrating between 9 kb and 23 kb are excised and eluted from the gel using β-agarase (New England Biolabs, Beverly Mass.). The eluted DNA fragments are ligated with BamHI-cleaved and dephosphorylated λ-EMBL4 vector arms, and the ligation mixtures are packaged using commercial packaging extracts (Stratagene, Lajolla, Calif.). The packaged DNA libraries are plated and amplified on *Escherichia coli* K802 cells. Approximately 10,000–20,000 plaques from each library are screened by plaque-hybridization with the radiolabeled lcc1 DNA fragment using the conditions described above. Plaques which give hybridization signals with the probe are purified twice on *E. coli* K802 cells, and DNA from the corresponding phage is purified from high titer lysates using a Qiagen Lambda kit (Qiagen, Inc., Chatsworth, Calif.).

3. Analysis of Laccase Genes

Restriction mapping of laccase clones is done using standard methods (Lewin, Genes. 2d ed., Wiley & Sons, 1985, New York). DNA sequencing is done with an Applied Biosystems Model 373A automated DNA Sequencer (Applied Biosystems, Inc., Foster City, Calif.) using the primer walking technique with dye-terminator chemistry (H. Giesecke et al., J. Virol. Methods 38: 47–60, 1992). Oligonucleotide sequencing primers are synthesized on an Applied Biosystems model 394 DNA/RNA Synthesizer.

B. RESULTS AND DISCUSSION

1. Identification of Laccase Gene Sequence

Total cellular DNA samples are prepared from the species *Neurospora crassa*, *Botrytis cinerea*, and *Myceliophthora*. Aliquots of these DNA preparations are digested with BamHI and fractionated by agarose gel electrophoresis. DNA in the gel is blotted to a Zeta-Probe™ membrane filter (BioRad Laboratories, Hercules, Calif.) and probed under conditions of mild stringency with a radiolabeled fragment encoding a portion of the *N. crassa* lcc1 gene, as described above. Laccase-specific sequences are detected in the genomes of *M. thermophila* and the *N. crassa* control, but not in the *B. cinerea* genomic DNA with this probe.

2. Cloning and Characterization of *Myceliophthora thermophila* Laccase (MtL) Gene Approximately 20,000 plaques from a *M. thermophila* genomic DNA library constructed in a λ-EMBL4 cloning vector are screened. The library is composed of approximately 10,000 independent clones with inserts ranging in size from 9 kb to 23 kb. Assuming an average insert size of 10 kb and a total genome size of $4 \times 10^7$ bp for *M. thermophila*, this figure is about 2.5 times the number of clones required to represent the entire genome. Eight plaques are identified that hybridized strongly to the *N. crassa* laccase gene probe. DNA is isolated from three of these, cleaved with EcoRI and analyzed by agarose gel electrophoresis and Southern hybridization. All three of these clones contain a 7.5 kb EcoRI fragment which hybridized to the laccase-specific probe. One of these EcoRI fragments is subcloned into pBR322 (Bolivar et al., Gene 2: 95–113, 1977) to generate plasmid pRaMB1. A restriction map of this DNA segment is shown in FIG. 1. The position of the laccase coding region on this clone is determined by hybridization with the lcc1 gene fragment described above. Based on mapping data obtained, and an estimated size of the laccase protein of approximately 80 kdal, it is reasoned that the entire *M. thermophila* laccase coding region is contained with a 3.2 kb NheI-BglII segment which is then subcloned into pUC119(Viera and Messing, Methods Enzymol. 153: 3–11, 1987). The nucleotide sequence of this segment is determined using the primer walking method (Giesecke et al., supra). The nucleic acid sequence is shown in FIG. 2 and SEQ ID NO: 1.

The deduced amino acid sequence of MtL is obtained on the basis of amino acid sequence homology with the *N. crassa* laccase. At the amino acid level, these two laccases share approximately 60% sequence identity. Similarity is highest in regions that correspond to the four histidines and one cysteine which are involved in the formation of the trinuclear copper cluster (Perry et al., J. Gen. Microbiol. 139: 1209–1218, 1993; Coll et al. Appl. Environ. Microbial. 59: 4129–4135, 1993; Messerschmidt et al. J. Mol. Biol. 206: 513–530, 1989). There are 11 potential sites for N-linked glycosylation in the deduced amino acid sequence of MtL the first 22 amino acids of MtL appear to comprise a canonical signal peptide with a predicted cleavage following an Ala residue (vonHeijne, J. Mol. Biol. 173:243–251, 1984). Although the amino terminal sequence of the native MtL is unknown, the amino terminus of recombinant MtL produced in *A. oryzae* is blocked with a pyro-glutamate residue. Enzymatic removal of this residue followed by amino acid sequencing suggests that mature MtL begins with a Gln residue (position 1 in FIG. 2; SEQ ID NO: 2). Thus, MtL is apparently synthesized as a 620 amino acid preproenzyme having a 22 amino acid signal peptide and propeptide of 25 residues. *Neurospora crassa* laccase(NcL) is processed similarly at its amino terminal end. In addition, NcL is also proteolytically processed at its C-terminus, resulting in the removal of 13 amino acids (Germann et al. J. Biol. Chem. 263: 885–896, 1988). The processing site is contained within the sequence Asp-Ser-Gly-Leu*Arg$_{558}$ (where * designates the cleavage site). A similar sequence exists near the C-terminal end of MtL(Asp-Ser-Gly-Leu-Lys$_{560}$), suggesting the Myceliophthora enzyme may also be subject to C-terminal processing (Asp-Ser-Gly-Leu*Lys$_{560}$) which would remove 12 amino acids.

The positions of six introns (85, 84, 102, 72, 147, and 93 nucleotides) within the lcc1 coding region are determined by comparing the deduced amino acid sequence of MtL to that of NcL and by applying the consensus rules for intron features in filamentous fungi (Gurr et al., in Gene Structure in Eukaryotic Microbes, J. R. Kinghorn, ed.) pp 93–139, IRL Press, Oxford, 1987). The 1860 nucleotides of coding sequence, excluding introns, are rich in guanosine and cytosine (65.5% G+C). The colon usage pattern for this gene reflects the DNA base composition in a strong bias(89.7%) for codons ending in G or C.

II. EXPRESSION OF MYCELIOPHTHORA LACCASE IN ASPERGILLUS

A. MATERIALS AND METHODS

1. Bacterial and Fungal Host Strains

*Escherichia coli* JM101(Messing et al., Nucl. Acids Res. 9:309–321, 1981) is used as a host for construction and routine propagation of laccase expression vectors in this study. Fungal hosts for laccase expression included the *Aspergillus niger* strains Bo-1, AB4.1 and AB1.13(Mattern et al., Mol. Gen. Genet. 234: 332–336), as well as a uridine-requiring (pyrG) mutant of the α-amylase-deficient *Aspergillus oryzae* strain HowB104.

2. Plasmids

Plasmid pRaMB2 is a pUC119 derivative which contains a 3.2 kb BglII-NheI fragment of *M. thermophila* genomic DNA encoding MtL. The vector pMWR is constructed by inserting the *A. oryzae* TAKA-amylase promoter and terminator elements from pTAKA17(Christensen et al., Bio/Technol. 6: 1419–1422, 1988; EP 238 023) into pUC18 (Yanisch-Perron et al., Gene 33: 103–119, 1985). In this vector, there is a unique SwaI site at the end of the promoter element and a single NsiI site at the beginning of the terminator for directional cloning of coding sequences. The cloning vehicle pUC518 is derived by inserting a small linker containing NsiI, ClaI, XhoI, and BglII restriction sites between the adjacent BamHI and XbaI sites of pUC118 (Vieira and Messing, supra). Plasmid pToC68(WO 91/17243) contains the *A. oryzae* TAKA-amylase promoter and *A. niger* glaA terminator, and pToC90(WO 91/17243) carries the *A. nidulans* amdS gene.

3. Construction of Laccase Expression Vectors

Figure 3:
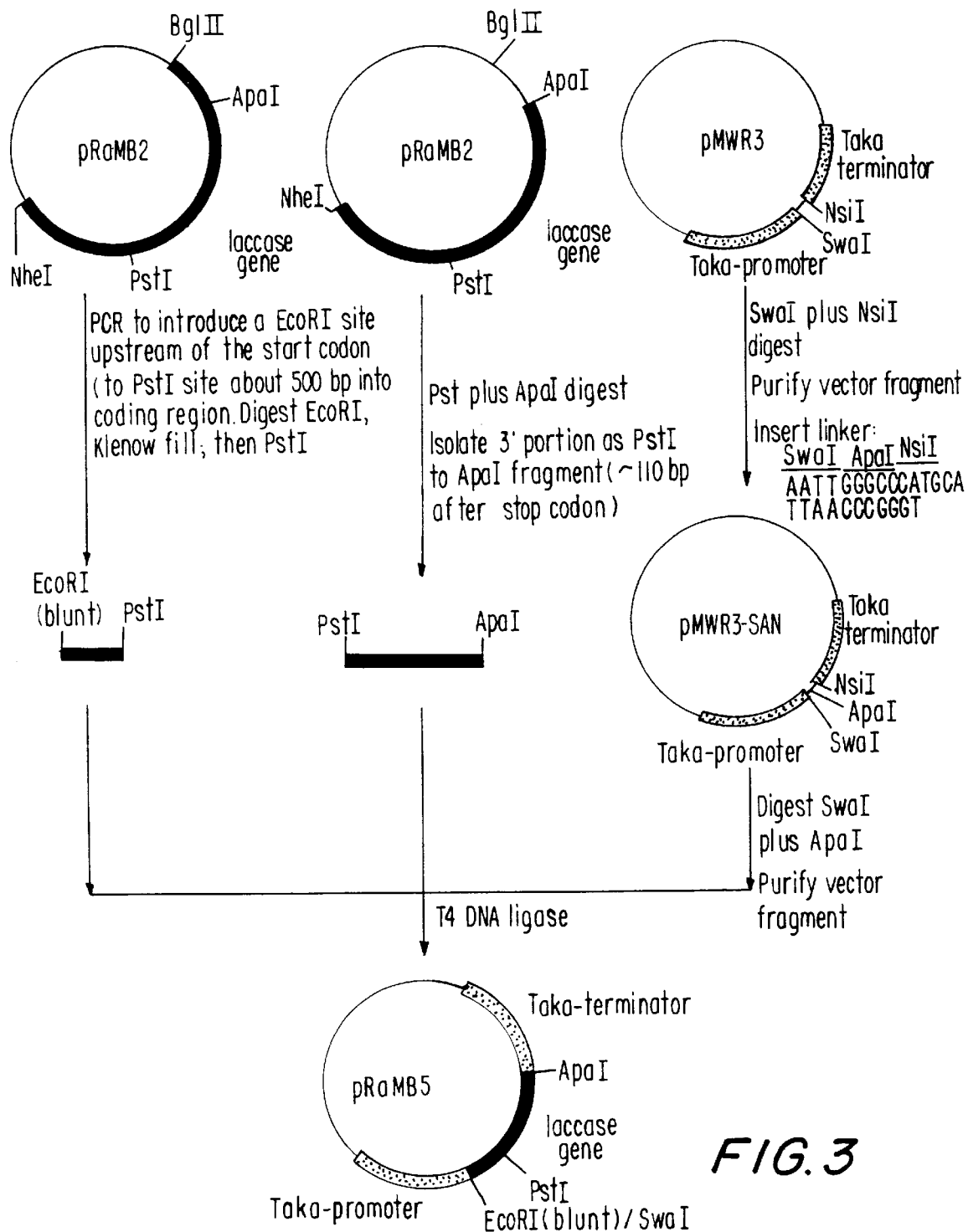
FIG. 3 illustrates the construction of plasmid pRaMB5.

The construction strategy for the laccase expression vector pRaMB5 is outlined in FIG. 3. The promoter directing transcription of the laccase gene is obtained from the *A. oryzae* α-amylase (TAKA-amylase) gene (Christensen et al., supra), as well as the TAKA-amylase terminator region. The plasmid is constructed first by modifying pMWR3 by inserting a small linker which contains an ApaI site between the SwaI and NsiI sites, creating a plasmid called pMWR3-SAN. PfuI polymerase-directed PCR (Stratagene, La Jolla, Calif.) is used to amplify a short DNA segment encoding the 5'-portion of MtL, from the start codon to an internal PstI site (approximately 0.5 kb). The forward primer for this PCR reaction is designed to create an EcoRI site just upstream of the start codon. Next, the amplified fragment is digested with EcoRI and PstI[during this step, the EcoRI site is made blunt by treatment with dNTPs and DNA polymerase I(Klenow fragment)] and purified by agarose gel electrophoresis. The 3' portion of the *M. thermophila* coding region is excised from pRaMB2 as a 2kb PstI-ApaI fragment(this segment also contains approximately 110 bp from the 3'-untranslated region). These two fragments are combined with SwaI- and ApaI-cleaved pMWR3-SAN in a three-part ligation reaction to generate the laccase expression vector pRaMB5.

4. Transformation of Aspergillus host cells

Methods for co-transformation of Aspergillus strains are as described in Christensen et al., supra. For introduction of the laccase expression vectors into *A. oryzae* HowB 104 pyrG, equal amounts (approximately 5 μg each) of laccase expression vector and one of the following plasmids are used: pPYRG (Fungal Genetics Stock Center, Kansas City, Kans.) which contains the *A. nidulans* pyrG gene(Oakley et al, Gene 61385–399, 1987); pSO2 which harbors the clones *A. oryzae* pyrG gene; pPRYG24 which contains the *A. ficuum*(=*A. niger*)pyrG gene. Protrophic(Pyr+) transformants are selected on Aspergillus minimal medium (Rowlands and Turner, Mol. Gen. Genet. 126: 201–216, 1973), and the transformants are transformants are screened for the ability to produce laccase on minimal medium containing 1 mM 2,2,'-azinobis(3-ethylbenzthiazolinesulfonic acid) [ABTS]. Cells which secrete active laccase oxidize the ABTS, producing a green halo surrounding the colony. Lastly, *A. niger* Bo-1 protoplasts are co-transformed using equal amounts (approximately 5 μg each) of laccase expression vector and pToC90 which contains the *A. nidulans* amdS (acetamidase) gene (Hynes et al., Mol. Cell Biol. 3: 1430–1439, 1983. AmdS+ transformants are selected on Cove minimal medium (Cove, Biochim. Biophys. Acta 113: 51–56, 1966) with 1% glucose as the carbon source and acetamide as the sole nitrogen source and screened for laccase expression on cove medium with 1 mM ABTS.

5. Analysis of Laccase-Producing Transformants

Transformants which produce laccase activity on agar plates are purified twice through conidiospores and spore suspensions in sterile 0.01% Tween-80 are made from each. The density of spores in each suspension is estimated spectrophotometrically ($A_{595}$ nm). Approximately 0.5 absorbance units of spores are used to inoculate 25 ml of ASPO4 or MY50 medium in 125 ml plastic flasks. The cultures are incubated at 37° C. with vigorous aeration (approximately 200 rpm) for four to five days. Culture broths are harvested by centrifugation and the amount of laccase activity in the supernatant is determined using syringaldazine as a substrate. Briefly, 800 μl of assay buffer (25 mM sodium acetate, pH 5.5, 40 μM $CuSO_4$) is mixed with 20 μl of culture supernatant and 60 μl of 0.28 mM syringaldazine (Sigma Chemical Co., St. Louis, Mo.) in 50% ETOH. The absorbance at 530 nm is measured over time in a Genesys 5 UV-vis spectrophotometer (Milton-Roy). One laccase unit(LACU) is defined as the amount of enzyme which oxidizes one μmole of substrate per minute at room temperature. SDS-polyacrylamide gel electrophoresis (PAGE) is done using precast 10–27% gradient gels from Novex(San Diego, Calif.). Protein bands are developed using Coomassie Brilliant Blue(Sigma).

B. RESULTS AND DISCUSSION

1. Expression of Myceliophthora laccase

Laccase-producing transformants are detected by incorporation of ABTS into selective media. Using pyrG or amdS as the selectable marker, co-transformation frequencies vary from about 30% to 70%. Heterologous expression of MtL appears to be highest in *A. oryzae* transformants. Furthermore, production appears to be better in ASPO4 medium compared to MY50, although the reasons for this are unknown. SDS-PAGE analysis of culture broth samples shows a prominent laccase band at approximately 80 kdal, which is similar to the size of the native enzyme purified from *M. thermophila*. Similar analysis of the culture filtrates from *A. niger* Bo-transformants indicate that the laccase band is obscured by very intense glucoamylase and acid-stable amylase protein bands. Results are shown in Table 1.

TABLE 1

MtL expression among selected *A. oryzae* and *A. niger* transformants

| HOST STRAIN | TRANSFORMANT | TRANSFORMING DNAS | MTLACU/ML ASPO4 | MY50 |
|---|---|---|---|---|
| *A. oryzae* HowB104 pyrG | untransformed | none | 0.00 | 0.00 |
| | RaMB5.15 | pRaMB5 + pPYRG | 0.85 | 0.29 |
| | RaMB5.30 | pRaMB5 + pPYRG | 0.71 | 0.87 |
| | RaMB5.33 | pRaMB5 + pPYRG | 0.60 | 0.26 |
| | RaMB5.108 | pRaMB5 + PSO2 | 0.68 | 0.19 |
| | RaMB5.111 | pRaMB5 + PSO2 | 0.70 | 0.17 |
| | RaMB5.121 | pRaMB5 + PSO2 | 0.49 | 0.20 |
| | RaMB5.142 | pRaMB5 + PSO2 | 0.54 | 0.04 |
| *A. Niger* Bo-1 | untransformed | none | 0.00 | 0.00 |
| | RaMB5.1 | pRaMB5 + pToC90 | n.d. | 0.20 |
| | RaMB5.25 | pRaMB5 + pToC90 | n.d. | 0.09 |
| | RaMB5.49 | pRaMB5 + pToC90 | n.d. | 0.06 |
| | RaMB5.51 | pRaMB5 + pToC90 | n.d. | 0.12 |
| | RaMB5.53 | pRaMB5 + pToC90 | n.d. | 0.21 |
| | RaMB5.62 | pRaMB5 + pToC90 | n.d. | 0.16 | n.d. = not determined

2. Expression in the presence or absence of excess copper

A 1 ml aliquot of a spore suspension of *Aspergillus oryzae* transformant HowB104-pRaMB5.30(approximately $10^9$ spores/ml) is added aseptically to a 500 ml shake flask containing 100 ml of sterile shake flask medium (maltose, 50 g/l; $MgSO_4.7H_2O$, 2 g/l; $KH_2PO_4$, 10 g/l; $K_2SO_4$, 2 g/l; $CaCl_2.2H_2O$ 0.5 g/l; Citric acid, 2 g/l; yeast extract, 10 g/l; trace metals[$ZnSO_4.7H_2O$, 14.3 g/l; $CuSO_4.5H_2O$, 2.5 g/l; $NiCl_2.6H_2O$, 0.5 g/l; $FeSO_4.7H_2O$, 13.8 g/l, $MnSO_4.H_2O$, 8.5 g/l; citric acid, 3.0 g/l], 0.5 ml/l; urea, 2 g/l, made with tap water and adjusted to pH 6.0 before autoclaving), and incubated at 37° C. on a rotary shaker at 200 rpm for 18 hours. 50 ml of this culture is aseptically transferred to a 3 liter fermentor containing 1.8 liters of the fermentor media ($MgSO_4.7H_2O$, 2 g/l; $KH_2PO_4$, 2 g/l; citric acid 4 g/l; $K_2SO_4$, 3 g/l; $CaCl_2.2H_2O$, 2 g/l; trace metals, 0.5 ml/l; pluronic antifoam, 1 ml/l). The fermentor temperature is maintained at 34° C. by the circulation of cooling water through the 20 fermentor jacket. Sterile air is sparged through the fermentor at a rate of 1.8 liter/min (1 v/v/m). The agitiation rate is maintained between 600 and 1300 rpm at approximately the minimum level required to maintain the dissolved oxygen level in the culture above 20%. Sterile feed (Nutriose 725[maltose syrup], 225 g/l; urea, 30 g/l; yeast extract, 15 g/l; pluronic antifoam, 1.5 ml/l, made up with distilled water and autoclaved) is added to the fermentor by use of a peristaltic pump. The feed rate profile during the fermentation is as follows: 30 g of feed is added initially before inoculation; 0–24 h, 2 g/l h; 24–48 h, 4 g/l h, 48 h-end, 6 g/l.

Copper is made as a 400× stock in water or a suitable buffer, filter sterilized and added aseptically to the tank to a final level of 0.5 mM. The fermentation described above is also conducted without the addition of copper supplement to tha tank medium. Samples for enzyme activity determination are withdrawn and filtered through Miracloth to remove mycelia. These samples are assayed for laccase activity by the LACU assay described above. Laccase activity is found to increase continuously during the course of the fermentation, with a value of approximately 45 LACU/ml achieved after 180 hours in the fermentation containing excess copper. At a specific activity of 22 LACU/mg, this corresponds to 2 g/l of recombinant laccase expressed. On the other hand, the maximum laccase activity achieved in the fermentation without copper supplement is approximately 10 LACU/ml after 170 hours, or about 25% of that found in the presence of additional copper.

III. PURIFICATION AND CHARACTERIZATION OF MYCELIOPHTHORA LACCASE

A. MATERIALS AND METHODS

1. Materials

Chemicals used as buffers and substrates are commercial products of at least reagent grade. Endo/N-glycosidase F and pyroglutamate amino peptidase are purchased from Boehringer Mannheim. Chromatography is performed on either a Pharmacia FPLC or a conventional low pressure system. Spectroscopic assays are conducted on either a spectrophotometer(Shimadzu PC160) or a microplate reader (Molecular Devices). Britton & Robinson(B&R) buffers are prepared according to the protocol described in Quelle, Biochemisches Taschenbuch, H. M. Raven, II. Teil, S.93 u. 102, 1964.

2. Enzymatic Assay

Laccase activity is determined by syringaldazine oxidation at 30° C. in a 1-cm quartz cuvette. 60 µl syringaldazine stock solution (0.28 mm in 50% ethanol) and 20 µl sample are mixed with 0.8 ml preheated buffer solution. The oxidation is monitored at 530 nm over 5 minutes. The activity is expressed as µmole substrate oxidized per minute. B&R buffers with various pHs are used. The activity unit is referred to here as "SOU". A buffer of 25 mM sodium acetate, 40 µM $CuSO_4$, pH 5.5, is also used to determine the activity, which is referred to as LACU, as defined above. 2,2'-azinobis(3-ethylbenzo thiazoline-6-sulfonic acid) (ABTS) oxidation assays are done using 0.4 mM ABTS, B&R buffer, pH 4.1, at room temperature by monitoring $\Delta A_{405}$. An ABTS oxidase activity overlay assay is performed by pouring cooled ABTS-agarose(0.05 g ABTS, 1 g agarose, 50 ml $H_2O$, heated to dissolve agarose) over a native IEF gel and incubating at room temperature. Thermostability analysis of the laccase(r-MtL) is performed using samples that have 3 SOU activity pre-incubated in B&R buffer, pH 6, at various temperatures. Samples are assayed after a 400-fold dilution into the same buffer at room temperature.

3. Purification from a fermentor broth 3.7 liters of cheese-cloth filtered broth (pH 7.6, 16 mS) is filtered through Whatman #2 filter paper. The broth is concentrated on a Spiral Concentrator (Amicon) with a S1Y100 membrane (MWCO:100) from 3700 ml to 200 ml. The concentrate is adjusted to 0.75 mS by diluting it in water and reconcentrated on S1Y100 to 170 ml. The washed and concentrated broth has a dense greenish color.

The broth is frozen overnight at −20° C., thawed the next day and loaded onto a Q-sepharose XK26 column (120 ml), pre-equilibrated with 10 mM Tris, pH 7.5, 0.7 mS(Buffer A). The blue laccase band migrates slowing down the column during loading. One group of blue fractions runs through the column after loading and washing by Buffer A. A second group eluted during the linear gradient with Buffer B (Buffer A plus 2 M NaCl). Some brown material with no laccase activity is eluted out later with 1 M NaOH. SDS-PAGE analysis shows that this preparation results in pure laccase.

4. Analyses of amino acid content, extent of glycosylation, and N-terminal sequence N-terminal sequencing is performed on an ABI 476A sequencer. Total amino acid analysis, from which the extinction coefficient of r-MtL is determined, is performed on a HP AminoQuant instrument. Deglycosylation is done using endo/N-glucosidase F according to the manufacturer's instructions and carbohydrate content is estimated by mobility difference as determined on SDS-PAGE. N-terminus de-blocking with pyroglutamate amino peptidase is carried out according to manufacturer's instructions. About 80 µg r-MtL is treated with 4 µg peptidase with or without the presence of 1 M urea or 0.1 M guanidine HCl before being blotted on a PVDF membrane for sequencing. About 20 pmol de-blocked protein is obtained and sequenced.

SDS-PAGE and native IEF analysis are performed on either a Novex cell or a Mini Protean II and a Model 111 Mini IEF cells (Bio-Rad). Gel filtration analyses are done on a Sephacryl S-300(Pharmacia), from which the native Mw is estimated by using Blue Dextran (2000 kdal), bovine IgG (158 kdal), bovine serum albumin (66 kdal), ovalbumin (45 kdal) and horse heart myoglobin(17 kdal) to calibrate the column.

B. RESULTS AND DISCUSSION

1. Purification and characterization of r-MtL from a fermentor broth

From 3.7 l of fermentor broth, about 2–3 g of r-MtL are isolated. Initial concentration using a membrane with MWCO of 100 kdal removed significant amounts of brown material and small contaminant proteins. The low affinity of r-MtL toward Q-Sepharose matrix equilibrated with 10 mM Tris, pH 7.5, facilitates its separation from other more acidic and more tightly bound impurities. As shown by SDS-PAGE, this preparation resulted in essentially pure laccase for the most active fractions located around the peak. Other less active fractions can be further purified on either mono-Q with a shallower gradient or a gel filtration column, such as S-300, from which the contaminants are separated due to their smaller MW. An overall 18-fold purification and a recovery of 67% are achieved. As discussed below, the existence of two elution bands of r-MtL on Q-Sepharose chromatogram is probably due to a differential glycosylation.

The purified r-MtL shows a MW of 100–140 kdal on S-300 gel filtration and a MW of 85 kdal on SDS-PAGE. The increase of r-MtL mobility on SDS-PAGE after deglycosylation suggests that carbohydrates account for 14% of its total mass. Native IEF shows a major band at pI ~4.2 that is active in ABTS overlay assay.

Directly sequencing the N-terminus of the purified r-MtL from samples either in desalted solution or on PVDF membrane are unsuccessful. However, treatment of r-MtL with pyroglutamate amino peptidase yielded a protein with deblocked N-terminus. This suggests the processing of a propeptide during the maturation of r-MtL, a posttranslational event similar to that of *N. crassa* laccase but not found in other laccases such as *Rhizoctonia solani*. The proposed scheme is outlined below.

```
MKSFISAATLWIVGILTPSVAAAPPSTEPQRDLLVPITEREEAAVKARQQSCNTPS
|<-putative signal ->  |<-  putative       ->|<-N-terminus
      peptide                propeptide
```

The spectrum of the blue r-MtL has absorption maxima at 276 and 589 nm.

The activity of the laccase is tested by using either syringaldazine and ABTS as substrates. Expressed as per $Abs_{276}$ or per mg, the laccase has a value of 20 or 45 units for SOU at pH 6.5, respectively. The LACU assay yields a value of 10 or 22 units per $Abs_{276}$ or per mg.

The pH profile of r-MtL activity is quite close to that of the wild type, with an optimal pH of 6.5. The upper temperature limit for retaining full activity after a 20 minute preincubation observed for r-MtL is approximately 60° C. The purified r-MtL shows no activity loss over a 5 week storage frozen in Q-sepharose elution buffer at −20° C.

When comparing the two forms of r-MtL obtained from the fermentor broth isolated on Q-Sepharose, there are no significant differences seen in terms of SDS-PAGE, native PAGE, native IEF, S-300 gel filtration, UV-visible spectrum, specific activity towards syringaldazine and ABTS, and deblocked N-terminus sequencing measurements. Likely, the different elution pattern on Q-Sepharose arises from some sort of differential glycosylation.

IV. USE OF MYCELIOPHTHORA LACCASE IN DYEING HAIR

The dyeing effect of Myceliophthora laccase is tested on various dye precursors and further on 0.1% p-phenylenediamine compared with a number of modifiers.

Materials:

Dye precursors:

0.1% p-phenylene-diamine in 0.1 M K-phosphate buffer, pH=7.0)

0.1% o-aminophenol in 0.1 M K-phosphate buffer, pH=7.0)

Enzymes:

Recombinant *Myceliophthora thermophila* laccase, 16 LACU/ml (in final dye solution).

Equipment:

Datacolor Textflash 2000 (CIE-Lab)

Assessment of the hair color

The quantitative color of the hair tresses is determined on a Datacolor Textflash 2000 by the use of CIE-Lab parameters L* ("0"=black and "100"=white) combined with a* ("−"= green and "+"=red).

Results:

Dyeing effect

Tresses of blond European hair (1 gram) are used for testing *Myceliophthora thermophila* laccase in the context of oxidative hair dyeing. p-phenylene diamine and o-aminophenol are used as the dye precursors.

Hair dyeing 4 ml dye precursor solution is mixed with 1 ml laccase on a Whirley mixer, applied to the hair tresses and kept at 30° C. for 60 minutes. The hair tresses are then rinsed with running water for about 3 minutes, pressed between two fingers, combed, and air dried.

The results of the dyeing effect test are displayed below in Table 1 and 2.

TABLE 1

| o-aminophenol | enzyme | L* | a* |
|---|---|---|---|
| Untreated blond hair | − | 70.3 | 2.3 |
| Laccase | + | 57.7 | 15.3 |

*: 0 = black, 100 = white
a*: − = green, + = red

TABLE 2

| p-phenylenediamine | enzyme | L* | a* |
|---|---|---|---|
| Untreated blond hair | − | 70.3 | 2.3 |
| 1.0 ml laccase | − | 29.1 | 4.1 |

L*: 0 = black, 100 = white
a*: − = green, + = red

Result of test:

From Table 1 and 2 it can be seen that the *Myceliophthora thermophila* laccase can be used for oxidative dyeing of hair.

Deposit of Biological Materials

The following biological materials have been deposited under the terms of the Budapest Treaty with the Agricultural Research Service Patent Culture Collection, Northern Regional Research Center, 1815 University Street, Peoria, Ill., 61604 on May 25, 1994, and given the following accession number.

| Deposit | Accession Number |
|---|---|
| *E. coli* JM101 containing pRaMB5 | NRRL B-21261 |

What we claim is:

1. A substantially purified laccase
comprising an amino acid sequence selected from the group consisting of the amino acid sequence set forth in SEQ ID NO:2, residues 23–620 of SEQ ID NO:2, and residues 48–620 of SEQ ID NO:2.

2. The laccase of claim 1, consisting of the amino acid sequence set forth in SEQ ID NO:2.

3. The laccase of claim 1, which is obtained from a Myceliophthora strain.

4. The laccase of claim 3, which is obtained from a Myceliophthora thermophila strain.

5. The laccase of claim 1, having a specific activity of at least 30 SOU/mg protein on syringaldazine as substrate at optimum pH.

6. A substantially pure laccase which is encoded by the nucleic acid sequence contained in plasmid pRaMB5 contained in E. coli NRRL B-21261.

7. A dye composition comprising a laccase of claim 1 and at least one dye precursor capable of being oxidized by the laccase in the presence of a source of oxygen.

8. The dye composition of claim 7, wherein the laccase has a specific activity of at least 30 SOU/mg protein on syringaldazine as substrate at optimum pH.

9. The dye composition of claim 7, further comprising at least one dye coupler.

10. A dye composition comprising a laccase of claim 6 and at least one dye precursor capable of being oxidized by the laccase in the presence of a source of oxygen.

11. The dye composition of claim 10, wherein the laccase has a specific activity of at least 30 SOU/mg protein on syringaldazine as substrate at optimum pH.

12. The dye composition of claim 10, further comprising at least one dye coupler.

13. A container containing a dye composition according to claim 7.

14. A container containing a dye composition according to claim 10.

15. A purified recombinant laccase
comprising an amino acid sequence selected from the group consisting of the amino acid sequence set forth in SEQ ID NO:2, residues 23–620 of SEQ ID NO:2, and residues 48–620 of SEQ ID NO:2
wherein said laccase is purified from a fungal host cell transformed or transfected with a nucleic acid construct encoding said laccase.

16. The laccase of claim 15 wherein said laccase has a specific activity of at least 30 SOU/mg protein on syringaldazine as substrate at optimum pH.

17. The laccase of claim 15, which is obtained from a Myceliophthora strain.

18. The laccase of claim 15, wherein said fungal host cell is selected from the group consisting of Aspergillus and Fusarium.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 3183 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: join(586..831, 917..994, 1079..1090, 1193..1264,
          1337..2308, 2456..2524, 2618..3028)

(xi) SEQUENCE DESCRIPTION: SEQ ID NO:1:

```
GCTAGCTTCT TTGGTCACCG TCGTTTTCGC CCGCCCCCTC CCTCCTTCAA CCCCCTGAGT      60

AGTCGGCTAA GCGATCCTCA ATCTGGTCTT GTGAGGTCAC GTCCTCCAGC AGATGACAGT     120

TCATCGAGCG AGTGATCTCC ACCACCCAGA AGGGAGGGGG GATGCGCGCA TGCTCCAACA     180

TCCCTGGTGT CGCTAGAGAC GTCGCGGCAT CAGCCTTTTC ATCACACCGA GCACGTCCAC     240

GGACCGGCTC CTTTCACCCC CGCGTCCTCC GGAGGATTGA GTCACGATAT TTCGGGATGT     300

GGGAAGGGGG AGAGAAAGGA GGGGGGAGGG GCGGAAACAT GTTGGATACG AGCTGCGCCC     360

CTTTTTCAAC ATCGAGAACA GGAAGTCGTT GGTGTCGGCC GTAATGTCTA TAAAACGAGG     420

CTCCTTCTCG TCGTCGACTT GTCTCAGGTT CTCTCTCTCG TCCACACCAA GCCAGTCTTG     480

CCTGAGCCAC CTGAGCCACC TTCAACTCAT CATCTTCAGT CAAGTCGTTC ATTGACATTG     540

TGTCTCTCTT TCTATCGAGT CGGCTTCCCG GCCCTTCACC ACAAC ATG AAG TCC         594
                                                 Met Lys Ser
                                                   1

TTC ATC AGC GCC GCG ACG CTT TTG GTG GGC ATT CTC ACC CCT AGC GTT      642
Phe Ile Ser Ala Ala Thr Leu Leu Val Gly Ile Leu Thr Pro Ser Val
      5                  10                  15

GCT GCT GCC CCT CCA TCC ACC CCT GAG CAG CGC GAC CTG CTC GTC CCG      690
Ala Ala Ala Pro Pro Ser Thr Pro Glu Gln Arg Asp Leu Leu Val Pro
 20                  25                  30                  35

ATC ACG GAG AGG GAG GAG GCA GCC GTG AAG GCT CGC CAG CAG AGC TGC      738
Ile Thr Glu Arg Glu Glu Ala Ala Val Lys Ala Arg Gln Gln Ser Cys
                 40                  45                  50

AAC ACC CCC AGC AAC CGG GCG TGC TGG ACT GAC GGA TAC GAC ATC AAC      786
Asn Thr Pro Ser Asn Arg Ala Cys Trp Thr Asp Gly Tyr Asp Ile Asn
             55                  60                  65

ACC GAC TAC GAA GTG GAC AGC CCG GAC ACG GGT GTT GTT CGG CCG          831
Thr Asp Tyr Glu Val Asp Ser Pro Asp Thr Gly Val Val Arg Pro
         70                  75                  80

GTGAGTGCTC TCGTTAATTA CGCTTCGGCG AGTTGCGCAG ATATATTAAA TACTGCAAAC     891

CTAAGCAGGA GCTGACATGC GACAG TAC ACT CTG ACT CTC ACC GAA GTC GAC      943
                            Tyr Thr Leu Thr Leu Thr Glu Val Asp
                                         85                  90

AAC TGG ACC GGA CCT GAT GGC GTC GTC AAG GAG AAG GTC ATG CTG GTT      991
Asn Trp Thr Gly Pro Asp Gly Val Val Lys Glu Lys Val Met Leu Val
             95                 100                 105

AAC GTACGGCACC CCTTTTCTTG TCCTAGGATC TGGGTGATGT GCGTCGTTGC          1044
Asn
```

```
CCCTGAGAGA GACTGACCGA GCCTTTGGCT GCAG AAT AGT ATA ATC GTAATTAATT        1100
                                    Asn Ser Ile Ile
                                        110

ATACCGCCCT GCCTCCAGCA GCCCCAGCAG CTCGAGAAGG GTATCTGAAG TTAGTCAGGC        1160

CTGCTGACCT GACCGGGGCC AACCCACCAT AG GGA CCA ACA ATC TTT GCG GAC          1213
                                    Gly Pro Thr Ile Phe Ala Asp
                                            115

TGG GGC GAC ACG ATC CAG GTA ACG GTC ATC AAC AAC CTC GAG ACC AAC          1261
Trp Gly Asp Thr Ile Gln Val Thr Val Ile Asn Asn Leu Glu Thr Asn
120                 125                 130                 135

GGC GTATGTCTGC TGCTTGCTCT CTTGCTCTCC TCGTCCGCGA CTAATAATAA               1314
Gly

TATCAACTCG TGTGGAAAAC AG ACG TCG ATC CAC TGG CAC GGA CTG CAC CAG         1366
                      Thr Ser Ile His Trp His Gly Leu His Gln
                                140                 145

AAG GGC ACC AAC CTG CAC GAC GGC GCC AAC GGT ATC ACC GAG TGC CCG          1414
Lys Gly Thr Asn Leu His Asp Gly Ala Asn Gly Ile Thr Glu Cys Pro
            150                 155                 160

ATC CCG CCC AAG GGA GGG AGG AAG GTG TAC CGG TTC AAG GCT CAG CAG          1462
Ile Pro Pro Lys Gly Gly Arg Lys Val Tyr Arg Phe Lys Ala Gln Gln
        165                 170                 175

TAC GGG ACG AGC TGG TAC CAC TCG CAC TTC TCG GCC CAG TAC GGC AAC          1510
Tyr Gly Thr Ser Trp Tyr His Ser His Phe Ser Ala Gln Tyr Gly Asn
180                 185                 190

GGC GTG GTC GGG GCC ATT CAG ATC AAC GGG CCG GCC TCG CTG CCG TAC          1558
Gly Val Val Gly Ala Ile Gln Ile Asn Gly Pro Ala Ser Leu Pro Tyr
195                 200                 205                 210

GAC ACC GAC CTG GGC GTG TTC CCC ATC AGC GAC TAC TAC TAC AGC TCG          1606
Asp Thr Asp Leu Gly Val Phe Pro Ile Ser Asp Tyr Tyr Tyr Ser Ser
            215                 220                 225

GCC GAC GAG CTG GTG GAA CTC ACC AAG AAC TCG GGC GCG CCC TTC AGC          1654
Ala Asp Glu Leu Val Glu Leu Thr Lys Asn Ser Gly Ala Pro Phe Ser
        230                 235                 240

GAC AAC GTC CTG TTC AAC GGC ACG GCC AAG CAC CCG GAG ACG GGC GAG          1702
Asp Asn Val Leu Phe Asn Gly Thr Ala Lys His Pro Glu Thr Gly Glu
    245                 250                 255

GGC GAG TAC GCC AAC GTG ACG CTC ACC CCG GGC CGG CGG CAC CGC CTG          1750
Gly Glu Tyr Ala Asn Val Thr Leu Thr Pro Gly Arg Arg His Arg Leu
260                 265                 270

CGC CTG ATC AAC ACG TCG GTC GAG AAC CAC TTC CAG GTC TCG CTC GTC          1798
Arg Leu Ile Asn Thr Ser Val Glu Asn His Phe Gln Val Ser Leu Val
275                 280                 285                 290

AAC CAC ACC ATG ACC ATC ATC GCC GCC GAC ATG GTG CCC GTC AAC GCC          1846
Asn His Thr Met Thr Ile Ile Ala Ala Asp Met Val Pro Val Asn Ala
            295                 300                 305

ATG ACG GTC GAC AGC CTC TTC CTC GGC GTC GGC CAG CGC TAC GAT GTC          1894
Met Thr Val Asp Ser Leu Phe Leu Gly Val Gly Gln Arg Tyr Asp Val
        310                 315                 320

GTC ATC GAA GCC AGC CGA ACG CCC GGG AAC TAC TGG TTT AAC GTC ACA          1942
Val Ile Glu Ala Ser Arg Thr Pro Gly Asn Tyr Trp Phe Asn Val Thr
    325                 330                 335

TTT GGC GGC GGC CTG CTC TGC GGC GGC TCC AGG AAT CCC TAC CCG GCC          1990
Phe Gly Gly Gly Leu Leu Cys Gly Gly Ser Arg Asn Pro Tyr Pro Ala
340                 345                 350

GCC ATC TTC CAC TAC GCC GGC GCC CCC GGC GGC CCG CCC ACG GAC GAG          2038
Ala Ile Phe His Tyr Ala Gly Ala Pro Gly Gly Pro Pro Thr Asp Glu
355                 360                 365                 370

GGC AAG GCC CCG GTC GAC CAC AAC TGC CTG GAC CTC CCC AAC CTC AAG          2086
Gly Lys Ala Pro Val Asp His Asn Cys Leu Asp Leu Pro Asn Leu Lys
            375                 380                 385
```

```
CCC GTC GTG GCC CGC GAC GTG CCC CTG AGC GGC TTC GCC AAG CGG CCC         2134
Pro Val Val Ala Arg Asp Val Pro Leu Ser Gly Phe Ala Lys Arg Pro
            390                 395                 400

GAC AAC ACG CTC GAC GTC ACC CTC GAC ACC ACG GGC ACG CCC CTG TTC         2182
Asp Asn Thr Leu Asp Val Thr Leu Asp Thr Thr Gly Thr Pro Leu Phe
        405                 410                 415

GTC TGG AAG GTC AAC GGC AGC GCC ATC AAC ATC GAC TGG GGC AGG CCC         2230
Val Trp Lys Val Asn Gly Ser Ala Ile Asn Ile Asp Trp Gly Arg Pro
420                 425                 430

GTC GTC GAC TAC GTC CTC ACG CAG AAC ACC AGC TTC CCA CCC GGG TAC         2278
Val Val Asp Tyr Val Leu Thr Gln Asn Thr Ser Phe Pro Pro Gly Tyr
435                 440                 445                 450

AAC ATT GTC GAG GTG AAC GGA GCT GAT CAG GTAAGAAAAA GGGGACCGCA           2328
Asn Ile Val Glu Val Asn Gly Ala Asp Gln
                455                 460

GGGGTGCTGC TGCAAGTACA CCTTGCTCGC CCTCCTGTTC TTCCTTAATA ACTACCTCCC       2388

AACCCTCCCC CCTAATTAAT TCACTTTAAA GGCCGATCAA GACTGACCGA GCCCCCTCTC       2448

TTTGCAG TGG TCG TAC TGG TTG ATC GAG AAC GAT CCC GGC GCA CCT TTC        2497
        Trp Ser Tyr Trp Leu Ile Glu Asn Asp Pro Gly Ala Pro Phe
                            465                 470

ACC CTA CCG CAT CCG ATG CAC CTG CAC GTAAGTTGGA TACATATATA               2544
Thr Leu Pro His Pro Met His Leu His
475                 480

TATATATATA TACATTGCTT TCCTGGCTCG CTCCCTTAAA TAAAATTAAA TAACCAAAAA       2604

TAACAAAAAA AAG GGC CAC GAC TTT TAC GTG CTG GGC CGC TCG CCC GAC         2653
            Gly His Asp Phe Tyr Val Leu Gly Arg Ser Pro Asp
                    485                 490                 495

GAG TCG CCG GCA TCC AAC GAG CGG CAC GTG TTC GAT CCG GCG CGG GAC         2701
Glu Ser Pro Ala Ser Asn Glu Arg His Val Phe Asp Pro Ala Arg Asp
                500                 505                 510

GCG GGC CTG CTG AGC GGG GCC AAC CCT GTG CGG CGG GAC GTG ACG ATG         2749
Ala Gly Leu Leu Ser Gly Ala Asn Pro Val Arg Arg Asp Val Thr Met
            515                 520                 525

CTG CCG GCG TTC GGG TGG GTG GTG CTG GCC TTC CGG GCC GAC AAC CCG         2797
Leu Pro Ala Phe Gly Trp Val Val Leu Ala Phe Arg Ala Asp Asn Pro
        530                 535                 540

GGC GCC TGG CTG TTC CAC TGC CAC ATC GCC TGG CAC GTC TCG GGC GGC         2845
Gly Ala Trp Leu Phe His Cys His Ile Ala Trp His Val Ser Gly Gly
545                 550                 555

CTG GGC GTC GTC TAC CTC GAG CGC GCC GAC GAC CTG CGC GGG GCC GTC         2893
Leu Gly Val Val Tyr Leu Glu Arg Ala Asp Asp Leu Arg Gly Ala Val
560                 565                 570                 575

TCG GAC GCC GAC GCC GAC GAC CTC GAC CGC CTC TGC GCC GAC TGG CGC         2941
Ser Asp Ala Asp Ala Asp Asp Leu Asp Arg Leu Cys Ala Asp Trp Arg
                580                 585                 590

CGC TAC TGG CCT ACC AAC CCC TAC CCC AAG TCC GAC TCG GGC CTC AAG         2989
Arg Tyr Trp Pro Thr Asn Pro Tyr Pro Lys Ser Asp Ser Gly Leu Lys
            595                 600                 605

CAC CGC TGG GTC GAG GAG GGC GAG TGG CTG GTC AAG GCG TGAGCGAAGG         3038
His Arg Trp Val Glu Glu Gly Glu Trp Leu Val Lys Ala
        610                 615                 620

AGGAAAAAGG AAACAAAGAG GGGGGGGGGG GCTAGTTCCT ATTTTTGCTT TTTTTTTTTG       3098

TTCTTGTCCT TGTGCTGGCG GTTACCCTGG TAAAGGAGAA GGGGGCCCCA AGTTCGAGTG       3158

GGTGTGTGAT CGGGTAAATA TTATC                                             3183
```

(2) INFORMATION FOR SEQ ID NO:2:

-continued

```
    (i) SEQUENCE CHARACTERISTICS:
         (A) LENGTH: 620 amino acids
         (B) TYPE: amino acid
         (D) TOPOLOGY: linear (ii) MOLECULE TYPE: protein (xi) SEQUENCE DESCRIPTION: SEQ ID NO:2:

Met Lys Ser Phe Ile Ser Ala Ala Thr Leu Leu Val Gly Ile Leu Thr
1               5                   10                  15

Pro Ser Val Ala Ala Pro Pro Ser Thr Pro Glu Gln Arg Asp Leu
            20                  25                  30

Leu Val Pro Ile Thr Glu Arg Glu Ala Ala Val Lys Ala Arg Gln
            35                  40                  45

Gln Ser Cys Asn Thr Pro Ser Asn Arg Ala Cys Trp Thr Asp Gly Tyr
    50                  55                  60

Asp Ile Asn Thr Asp Tyr Glu Val Asp Ser Pro Asp Thr Gly Val Val
65                  70                  75                  80

Arg Pro Tyr Thr Leu Thr Leu Thr Glu Val Asp Asn Trp Thr Gly Pro
                85                  90                  95

Asp Gly Val Val Lys Glu Lys Val Met Leu Val Asn Asn Ser Ile Ile
                100                 105                 110

Gly Pro Thr Ile Phe Ala Asp Trp Gly Asp Thr Ile Gln Val Thr Val
                115                 120                 125

Ile Asn Asn Leu Glu Thr Asn Gly Thr Ser Ile His Trp His Gly Leu
130                 135                 140

His Gln Lys Gly Thr Asn Leu His Asp Gly Ala Asn Gly Ile Thr Glu
145                 150                 155                 160

Cys Pro Ile Pro Pro Lys Gly Gly Arg Lys Val Tyr Arg Phe Lys Ala
                165                 170                 175

Gln Gln Tyr Gly Thr Ser Trp Tyr His Ser His Phe Ser Ala Gln Tyr
                180                 185                 190

Gly Asn Gly Val Val Gly Ala Ile Gln Ile Asn Gly Pro Ala Ser Leu
                195                 200                 205

Pro Tyr Asp Thr Asp Leu Gly Val Phe Pro Ile Ser Asp Tyr Tyr Tyr
    210                 215                 220

Ser Ser Ala Asp Glu Leu Val Glu Leu Thr Lys Asn Ser Gly Ala Pro
225                 230                 235                 240

Phe Ser Asp Asn Val Leu Phe Asn Gly Thr Ala Lys His Pro Glu Thr
                245                 250                 255

Gly Glu Gly Glu Tyr Ala Asn Val Thr Leu Thr Pro Gly Arg Arg His
                260                 265                 270

Arg Leu Arg Leu Ile Asn Thr Ser Val Glu Asn His Phe Gln Val Ser
                275                 280                 285

Leu Val Asn His Thr Met Thr Ile Ile Ala Ala Asp Met Val Pro Val
                290                 295                 300

Asn Ala Met Thr Val Asp Ser Leu Phe Leu Gly Val Gly Gln Arg Tyr
305                 310                 315                 320

Asp Val Val Ile Glu Ala Ser Arg Thr Pro Gly Asn Tyr Trp Phe Asn
                325                 330                 335

Val Thr Phe Gly Gly Gly Leu Leu Cys Gly Gly Ser Arg Asn Pro Tyr
                340                 345                 350

Pro Ala Ala Ile Phe His Tyr Ala Gly Ala Pro Gly Gly Pro Pro Thr
                355                 360                 365

Asp Glu Gly Lys Ala Pro Val Asp His Asn Cys Leu Asp Leu Pro Asn
370                 375                 380
```

```
Leu Lys Pro Val Val Ala Arg Asp Val Pro Leu Ser Gly Phe Ala Lys
385             390             395             400

Arg Pro Asp Asn Thr Leu Asp Val Thr Leu Asp Thr Thr Gly Thr Pro
            405             410             415

Leu Phe Val Trp Lys Val Asn Gly Ser Ala Ile Asn Ile Asp Trp Gly
            420             425             430

Arg Pro Val Val Asp Tyr Val Leu Thr Gln Asn Thr Ser Phe Pro Pro
            435             440             445

Gly Tyr Asn Ile Val Glu Val Asn Gly Ala Asp Gln Trp Ser Tyr Trp
            450             455             460

Leu Ile Glu Asn Asp Pro Gly Ala Pro Phe Thr Leu Pro His Pro Met
465             470             475             480

His Leu His Gly His Asp Phe Tyr Val Leu Gly Arg Ser Pro Asp Glu
            485             490             495

Ser Pro Ala Ser Asn Glu Arg His Val Phe Asp Pro Ala Arg Asp Ala
            500             505             510

Gly Leu Leu Ser Gly Ala Asn Pro Val Arg Arg Asp Val Thr Met Leu
            515             520             525

Pro Ala Phe Gly Trp Val Val Leu Ala Phe Arg Ala Asp Asn Pro Gly
530             535             540

Ala Trp Leu Phe His Cys His Ile Ala Trp His Val Ser Gly Gly Leu
545             550             555             560

Gly Val Val Tyr Leu Glu Arg Ala Asp Asp Leu Arg Gly Ala Val Ser
            565             570             575

Asp Ala Asp Ala Asp Asp Leu Asp Arg Leu Cys Ala Asp Trp Arg Arg
            580             585             590

Tyr Trp Pro Thr Asn Pro Tyr Pro Lys Ser Asp Ser Gly Leu Lys His
            595             600             605

Arg Trp Val Glu Glu Gly Glu Trp Leu Val Lys Ala
            610             615             620
```